United States Patent
Perkins et al.

(10) Patent No.: US 8,562,692 B2
(45) Date of Patent: Oct. 22, 2013

(54) DISTAL LOCK FOR A PROSTHETIC HARD SOCKET

(75) Inventors: Matt Perkins, Boise, ID (US); Travis Dean, Boise, ID (US)

(73) Assignee: Coyote Design and Manufacturing, Inc., Boise, ID (US)

( * ) Notice: Subject to any disclaimer, the term of this patent is extended or adjusted under 35 U.S.C. 154(b) by 228 days.

(21) Appl. No.: 13/104,937

(22) Filed: May 10, 2011

(65) Prior Publication Data

US 2011/0307080 A1    Dec. 15, 2011

Related U.S. Application Data

(60) Provisional application No. 61/333,167, filed on May 10, 2010.

(51) Int. Cl.
*A61F 2/80* (2006.01)

(52) U.S. Cl.
USPC ............................................. 623/34; 623/36

(58) Field of Classification Search
CPC .............................................. A61F 2002/7875
See application file for complete search history.

(56) References Cited

U.S. PATENT DOCUMENTS

| | | | |
|---|---|---|---|
| 1,586,015 A | 5/1926 | Underwood | |
| 2,530,285 A | 11/1950 | Catranis | |
| 2,533,404 A | 12/1950 | Sharp et al. | |
| 2,569,790 A | 10/1951 | White et al. | |
| 2,790,180 A | 4/1957 | Hauser | |
| 2,897,512 A | 8/1959 | Sackett | |
| 4,634,446 A | 1/1987 | Kristinsson | |
| 5,007,937 A | 4/1991 | Fishman et al. | |
| 5,201,774 A | 4/1993 | Greene | |
| 5,376,131 A | 12/1994 | Lenze et al. | |
| 5,507,834 A | 4/1996 | Laghi | |
| 5,507,837 A | 4/1996 | Laghi | |
| 5,658,353 A | 8/1997 | Layton | |
| 5,709,017 A | 1/1998 | Hill | |
| 5,888,215 A | 3/1999 | Roos et al. | |
| 5,888,234 A | 3/1999 | Littig | |
| 5,904,722 A | 5/1999 | Caspers | |
| 6,106,559 A | 8/2000 | Meyer | |
| 6,334,876 B1 | 1/2002 | Perkins | |
| 6,626,952 B2 | 9/2003 | Janusson et al. | |

(Continued)

FOREIGN PATENT DOCUMENTS

DE    10 2005 034 388 A1 *  12/2006

*Primary Examiner* — David H Willse
(74) *Attorney, Agent, or Firm* — Pedersen and Company, PLLC; Ken J. Pedersen; Barbara S. Pedersen

(57) ABSTRACT

A lock connects the distal end of a liner to the distal end of the hard socket of a prosthetic leg, and limits or prevents air flow into the hard socket through the distal lock mechanism, even when vacuum is established inside the socket. The distal lock normally is latched, but can be conveniently unlatched by swinging a cammed latch handle. The liner pin may be inserted and locked into the distal lock, without the distal lock being unlatched and without losing the internal air seal preventing air flow through passages of the lock. A slidable, biased lock blade, and interaction between slanted surfaces of the blade and the liner pin, allow the pin to slide down, but not up, past the blade. The latch handle does protrude radially outward a significant distance, when the lock is unlatched, but, as soon as the lock is latched, the handle resides against and/or near the outer surface of the lock housing.

17 Claims, 12 Drawing Sheets

(56) References Cited

U.S. PATENT DOCUMENTS

| | | |
|---|---|---|
| 6,706,364 B2 | 3/2004 | Janusson et al. |
| 7,427,298 B1 * | 9/2008 | Swanson, Sr. .................. 623/34 |
| 7,993,413 B2 | 8/2011 | Perkins et al. |
| 8,343,233 B2 | 1/2013 | Perkins et al. |

* cited by examiner

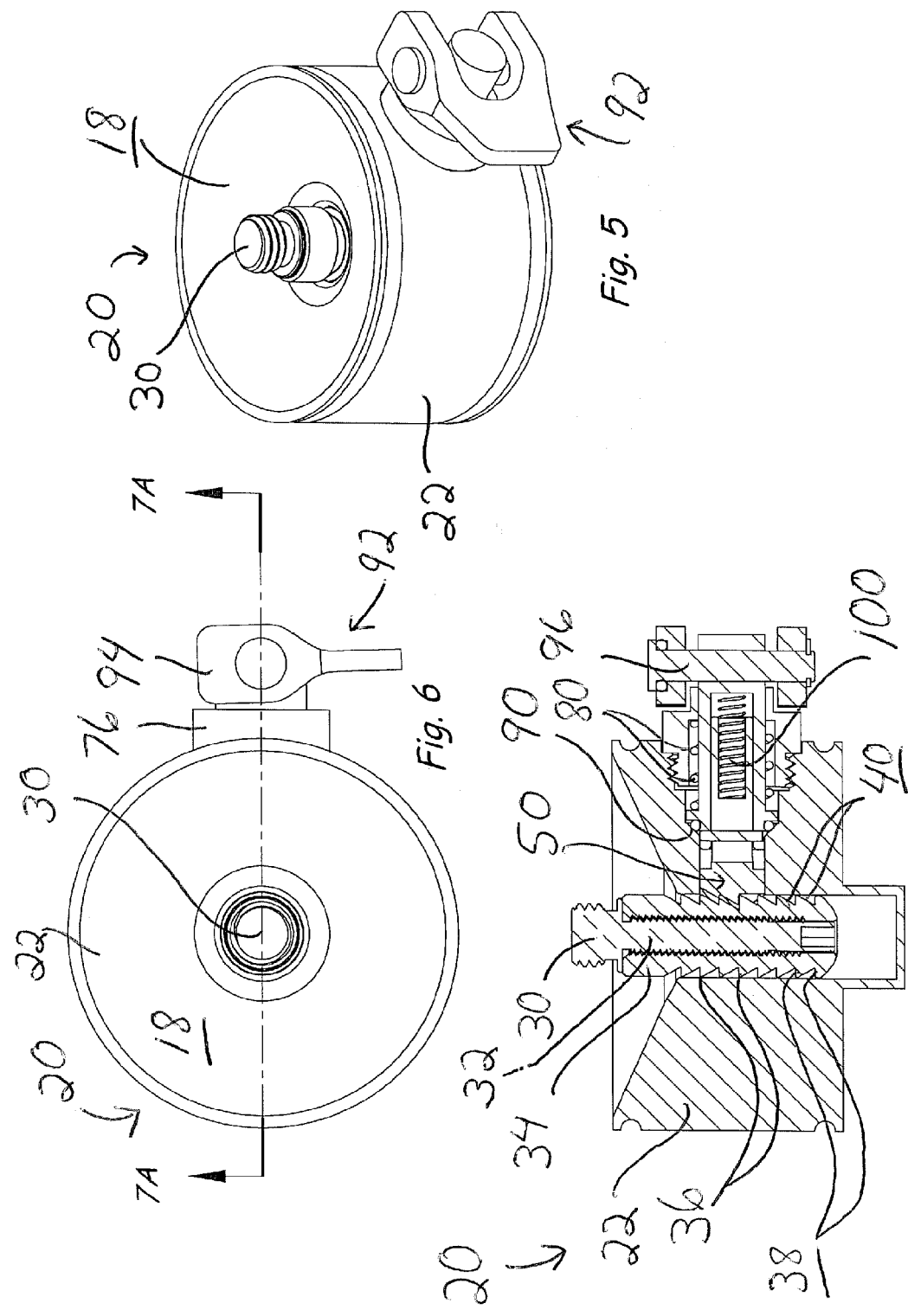

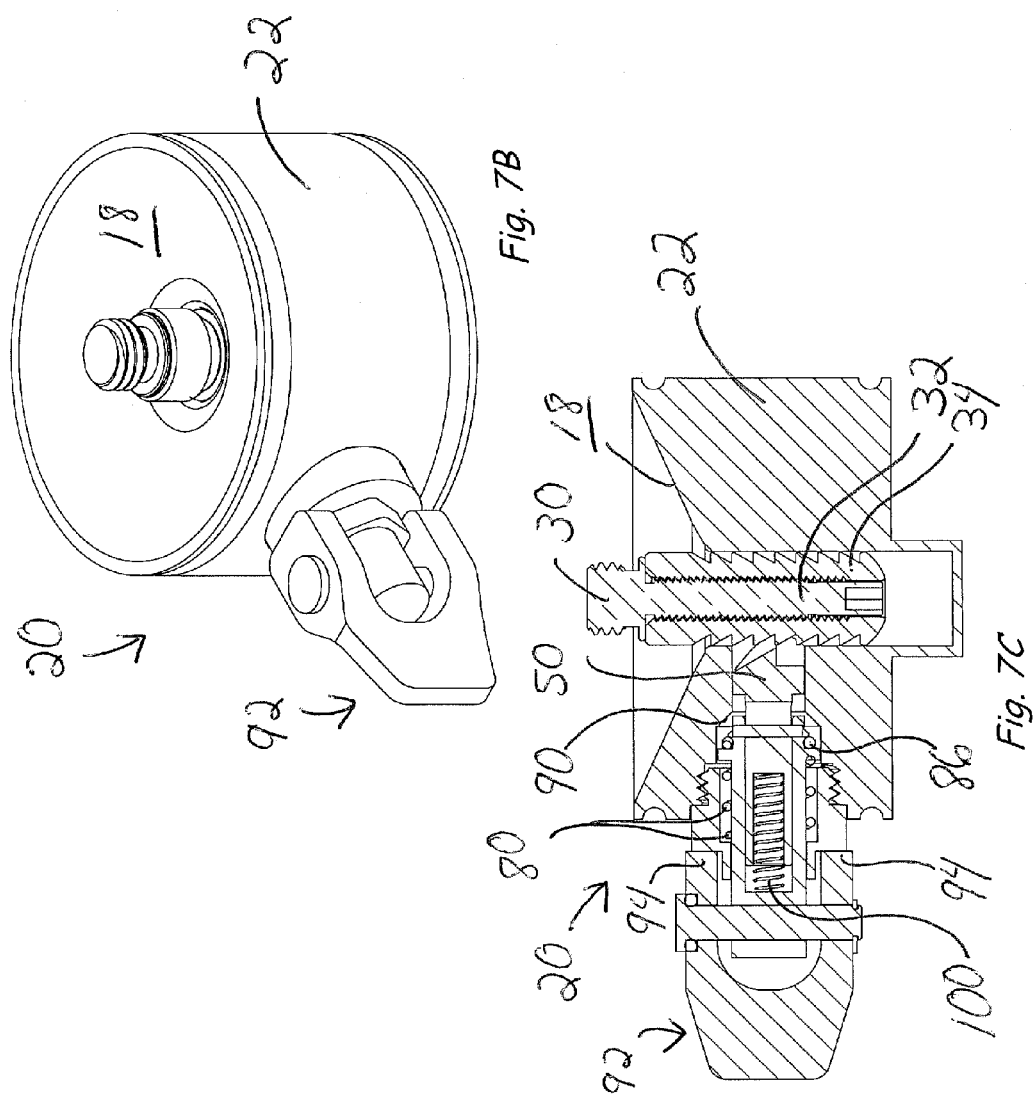

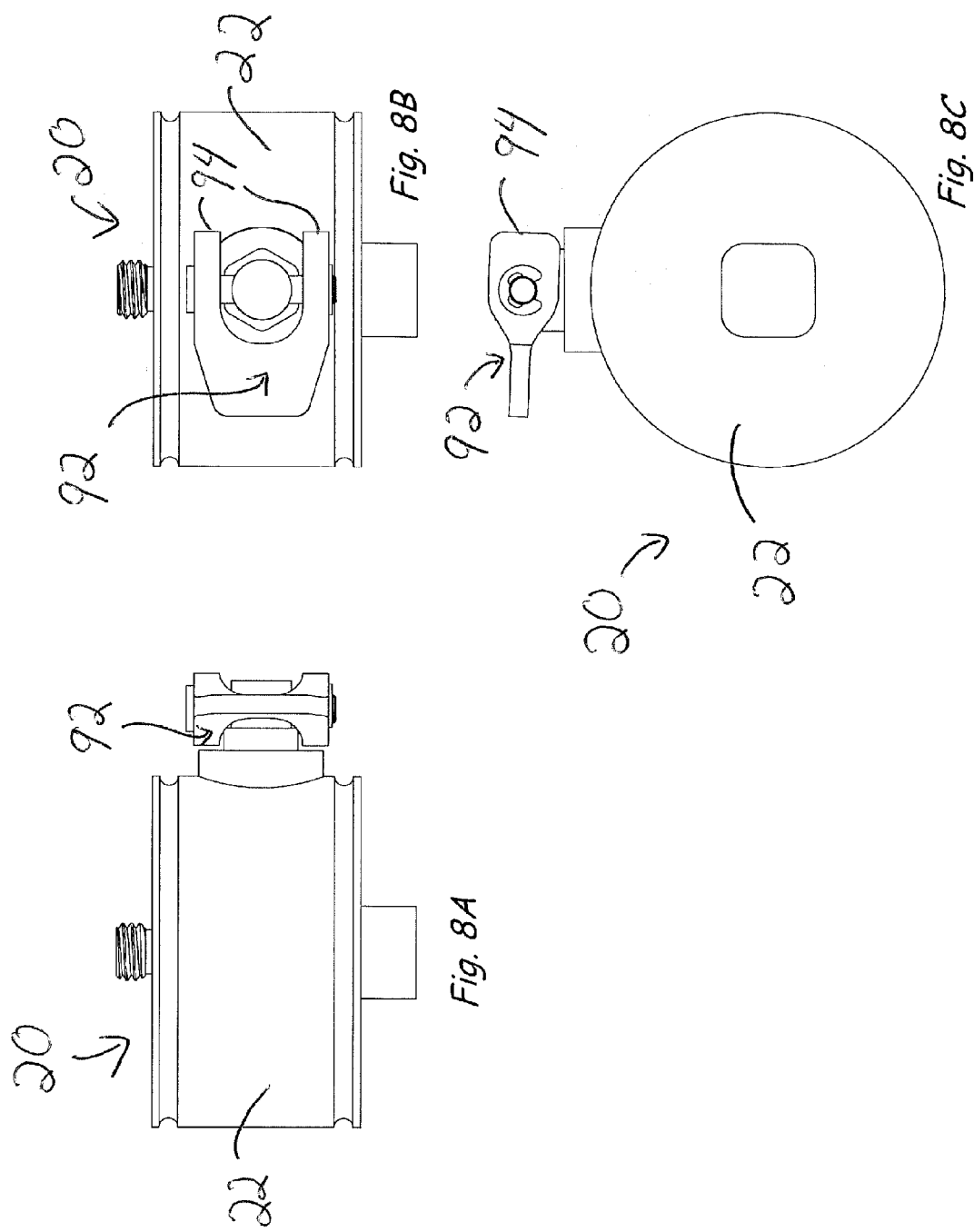

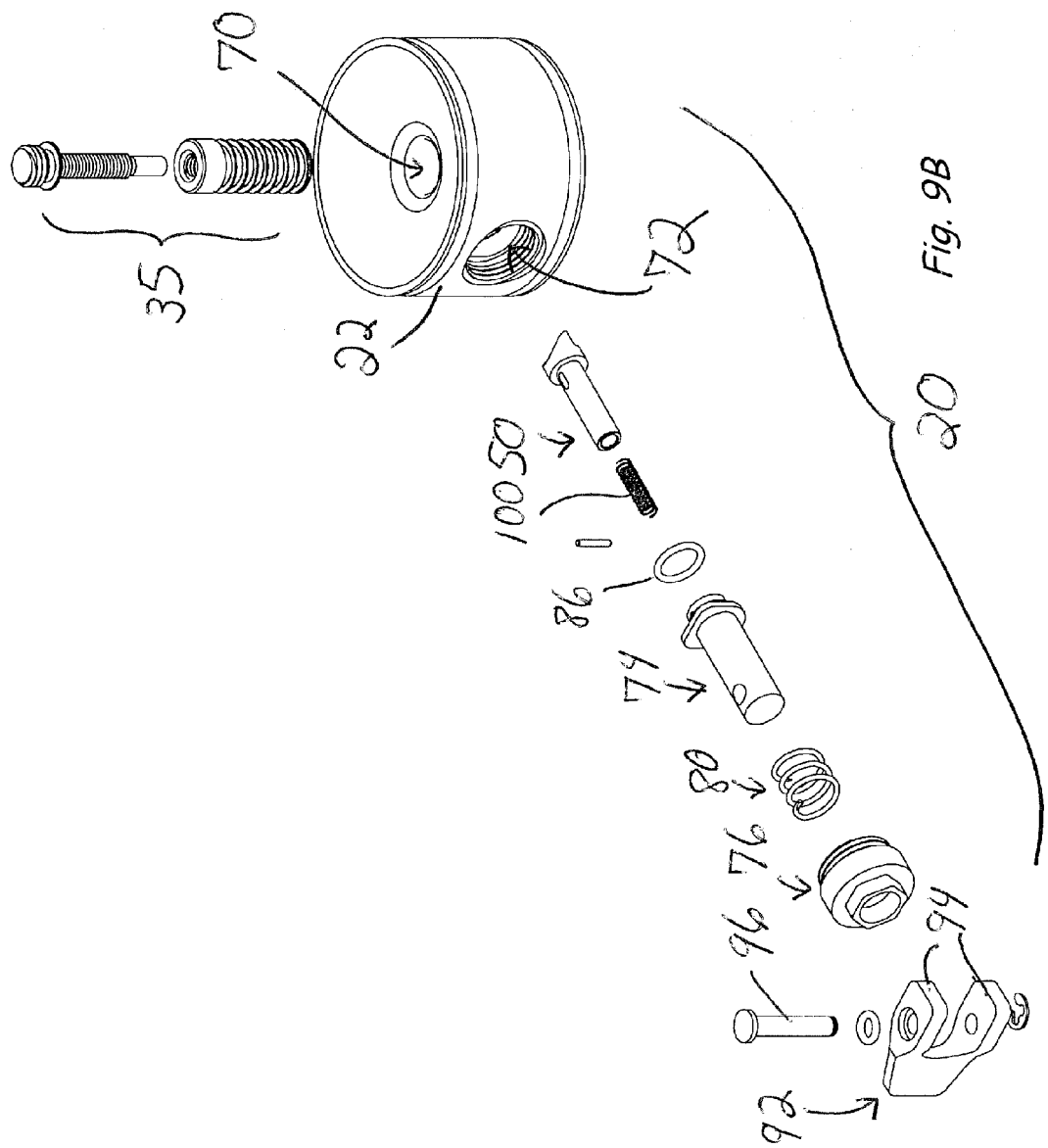

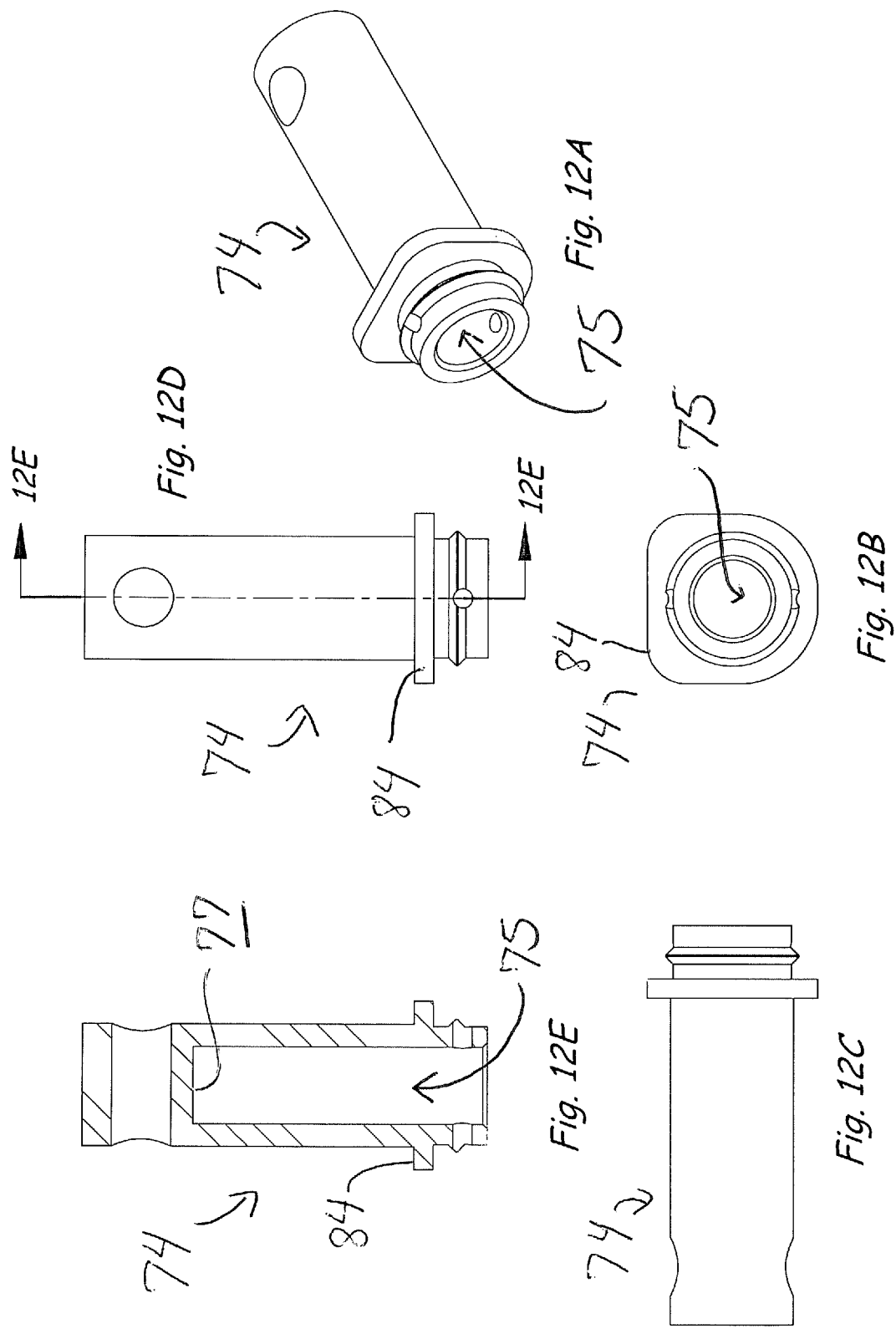

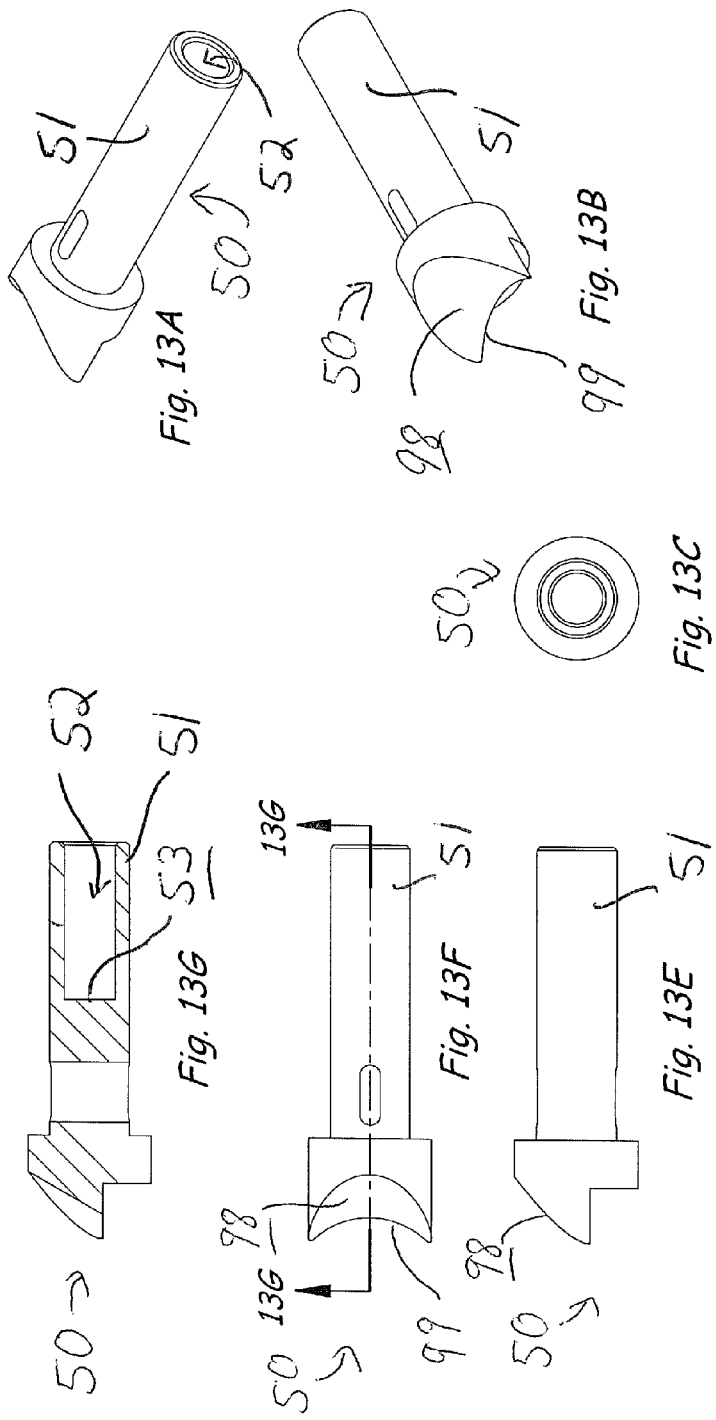

DISTAL LOCK FOR A PROSTHETIC HARD SOCKET

This application claims benefit of Provisional Application Ser. No. 61/133,167, filed May 10, 2010, the entire disclosure of which is incorporated herein by this reference.

BACKGROUND OF THE INVENTION

1. Field of the Invention

The present invention relates to external prosthetics, and more specifically to a lock system for securing a prosthetic hard socket to a socket liner worn on a residual limb. The preferred lock system connects the distal end of the liner to the distal end of the hard socket, and the preferred embodiments are adapted to prevent air flow into or out of the hard socket through the lock mechanism during normal use of the prosthetic limb. This way, pressure in the distal end of the interior well of the hard socket may be effectively controlled by other mechanisms, such as a vacuum pump and/or other mechanisms. When a vacuum fit is desired, as discussed elsewhere in this document, the pressure inside the hard socket may be controlled and adjusted accurately and reliably because air is not leaking into the hard socket through the lock mechanism. The lock is actuated by a lever system at or near the outer surface of the hard socket, wherein the lever may be easily swung to open and close the lock. Alternative embodiments do not prevent air flow into or out of the hard socket during normal use of the prosthetic limb, but are lever-actuated.

When in the latched configuration, the preferred lock mechanism locks a liner pin into a bore in the hard socket, wherein the liner pin is an elongated pin assembly or other shaft that protrudes downward from the distal end of the liner on the wearer's residual leg. When the wearer unlatches the preferred lock mechanism, with an easy and comfortable swing of the latch handle, the liner pin, and therefore, the liner and residual limb, are removable from the socket.

2. Related Art

Optimum connection/suspension methods for securing a prosthetic limb to a residual limb take into account several factors, including control, comfort, ease of donning and removal, and long term effects on the health of the skin and other tissue. These factors are weighed differently and influenced differently, depending on the wearer's residual limb, level of activity, and preferences. One reason that suspension solutions are not simple is that gravitational and other forces tend to cause separation between a prosthetic limb and a residual limb. This happens especially during the swing phase of the gait, when a prosthetic leg is additionally subjected to centrifugal forces. Patients have routinely worn a variety of belts, straps, cuffs and harnesses to prevent the prosthetic limb from separating from the residual limb, but such devices are inconvenient and tend to cause chafing against the patient's body, giving rise to sores and abrasions. Advanced methods of suspension have been developed, for example "suction" and "vacuum" suspension, proximal attachment systems, and distal lock mechanisms. These modern methods are made more effective by modern roll-on liners that are adapted to grip the residual limb, and that are also adapted to attach/connect to the hard socket by said proximal attachment systems, distal lock mechanisms, and/or by suction or vacuum, relative to ambient air, inside the distal end of the well of the hard socket.

As discussed in more detail below, "suction" is typically used for systems that establish a pressure inside the distal end of the well of the hard socket that is moderately lower than ambient. Suction systems typically do not utilize any pump or other mechanical device to pump air out of the well of the hard socket; instead, for example, they utilize the force of the limb pressing into the socket, plus an air expulsion valve, to lower pressure inside the well. Therefore suction systems typically operate in the range of ½-4.9 psi (and preferably 1-1.5 psi) lower than ambient. "Vacuum" systems, on the other hand, utilize a vacuum pump or other mechanical device to remove air from the well, and may establish an air pressure inside the well in the range of 1-14.7 psi below ambient. More typically, however, vacuum systems operate in a well pressure range lower than suction systems, for example 5-14.7 psi below ambient.

In summary, therefore, a suction suspension is typically established and maintained by exhausting air from the distal end of the well when the user dons the socket and during each portion of the user's gait that works to push the limb deeper inside the hard socket. Vacuum, on the other hand, is typically established and maintained by use of a vacuum pump connected to the well of the hard socket.

It has long been appreciated that differential air pressure, referred by those of skill in the art as "suction" (or as "vacuum" when greater differentials are established), may be utilized to retain or suspend, or assist in retaining or suspending, a prosthetic limb on a patient's residual limb. "Suction" or "vacuum" suspension typically involves a hard socket and a cooperating liner positioned between the residual limb and the prosthetic socket. Many modern hard sockets are intended to fit accurately and snugly to the residual limb, and they are often "molded" to the shape of the limb. This fit tends to create a close fit between the outer surface of the liner and the inner surface of the hard socket, in effect, sealing or partially sealing the liner to said inner surface around the circumference of the residual limb along a significant length of the residual limb. Donning the hard socket, therefore, involves inserting the limb and liner into the socket and releasing pressure that builds in the distal end of the socket well because the air inside the socket does not easily escape past the liner and out of the socket. This release may be accomplished by a hand-operated or automatic valve, vacuum pump, and/or other pressure release/control means. Because of the close molded fit of many hard sockets to the residual limb of today's wearers, a "suction" or "vacuum" suspension is possible whether the wearer uses a "first generation" liner that has gel-like inner and outer surfaces, or a "second generation" liner that has a gel-like inner surface and a fabric outer surface, as further discussed below.

Socket liners frequently have been called "suction liners," "gel liners," "roll-on liners" or "suspension liners" and include the "first generation" of gel-layer-only liners, and also the modern "second generation" of multi-layer liners that include an outer layer of fabric and that currently are preferred by most wearers of prosthetics. Socket liners are usually fabricated from silicone, urethane, or other gel-like material that grips the limb to such an extent that they need to be rolled-onto the limb from a rolled-up "doughnut" form, rather than pulled on like a sock. When rolled-on, there is little, if any, air remaining between the inner surface of the roll-on liner and the limb, and the roll-on liner is snug against the limb all the way around the circumference of the limb. Also, the inner surface of the roll-on liner is of such material and tacky texture that air will not be able to, or be very unlikely to, enter between the roll-on liner and limb. Thus, the roll-on liner may be said to form a suction fit and/or a slight compression fit with the limb. A distal force on the liner, such as caused by the swing of a gait with a prosthetic leg, may tug on the roll-on liner but typically does not loosen, lower, or remove the liner from the limb. The liner is difficult to remove except by rolling the top edge of the liner down off of the limb. Thus, longitudinal (axial) forces on the liner do not easily pull the liner out of place or off of the limb. The liners are therefore quite effective in their adhering and staying on the residual limb, and many of the other features of modern suspension systems therefore focus on connection of the hard socket to the liner, as is discussed later in this document.

First generation liners, which featured a gel layer contacting both the residual limb (liner's inner surface) and also the socket (liner's outer surface), can be used to create a fairly high amount of pressure differential between the inside of the socket (in the "well" of the socket) and the surrounding ambient air. This could be accomplished by releasing air pressure from the distal end of the socket well, for example, by a manual valve in the socket wall, after which a very good seal between the limb and the liner and the liner and the hard socket could be maintained by the gel liner. Modern "second generation" liners, comprising a thin textile/fabric outer layer that is fixed to the gel-like inside layer, are similar to the first generation regarding the connection to the residual limb, but are different regarding the connection/cooperation with, the socket. Because the outer fabric layer of the second generation liners is not as tacky as a gel layer, these second generation liners do not seal as thoroughly as the first generation liners to the inner surface of the hard socket, resulting in less gripping of the socket by the liner and some small amount (albeit it slow) air flow between the liner and the socket interior surface. However, even with these second generation liners, a "partial suction" suspension is still possible, by using air expulsion valves, for example, and a "vacuum" suspension is still possible by using a vacuum pump.

Thus, second generation liners more accurately may be said to allow only "partial suction" (unless a vacuum pump is employed) because the fabric layer(s) do not form what would be called "true" or "pure" suction with the socket. The terms "suction liner" and "suction socket" are still used by many manufacturers, prosthetic technicians, insurance and medicare/medicaid entities, and wearers of prosthetics. See the discussion of suction liners in Janusson, et al. (U.S. Pat. No. 6,706,364) and Janusson, et al. (U.S. Pat. No. 6,626,952). The second generation liners, and the "partial suction" suspension they typically provide, are more comfortable for many wearers than a "true suction fit" that is more likely to be obtained by a gel liner without a fabric layer, wherein a gel-seal is formed by the liner both to the limb and to the socket. When a vacuum suspension is needed, the hard socket may be fit with a vacuum pump and control system.

The terms "suction," "suction-fit," and "suction suspension" herein refer to the general process known well in this field of providing a "roll-on" liner or other "interference" liner that helps keep a socket on a residual limb while creating at least a small amount of blockage/hindrance to air freely moving in and out of the socket well past the residual limb, wherein the air moving is typically due to the action of the limb in the socket. A "vacuum suspension" herein describes suspensions that utilize a vacuum pump or other active mechanical device to actively establish and maintain a lower air pressure in the distal end of the interior well of the hard socket, for example, a pressure that is preferably 5-14.7 psi less than ambient air pressure. In another approach, "suction", "suction suspension" or "suction fit" may be defined as suspension/fittings that qualify under the medical code for "suction" and "vacuum", "vacuum suspension" or "vacuum fit" may be defined as suspension/fittings that qualify under the medical code for "vacuum".

Additional attachment systems may be used to supplement the suspension. One example is the distal lock of the instant inventors (Perkins, Coyote Design and Manufacturing, Inc.) in U.S. Pat. No. 6,334,876, issued Jan. 1, 2002, wherein a liner pin is locked into the distal end of the hard socket (see FIG. 4). In this Perkins device, a spring biases a plunger and an air-seal o-ring outward unless the wearer/assistant pushes the plunder radially inward. However, this Perkins device is not well-adapted for use with a vacuum system. If significant vacuum is established in the hard socket of this Perkins device, for example, with a vacuum pump, the vacuum will tend to pull the plunger and o-ring inward, thus undesirably unseating the o-ring and allowing air through the distal lock and into the socket.

Therefore, there is still a need for an improved distal lock system, especially for use in vacuum suspension systems. There is a need for such a distal lock system that does not break the vacuum established inside the hard socket, either during normal walking or during periods of sitting or resting. There is a need for such a distal lock system that is easy to use and that is reliable. There is a need for an improved lock actuation system that is easy and reliable to use with one hand or one finger, which may be used on a variety of prostheses including those for legs and arms, and which may be used in conjunction with vacuum, suction, or other attachment systems. The invention meets these needs.

SUMMARY OF THE INVENTION

The invention comprises a lock for connecting a limb liner to a hard socket of a prosthetic leg or of a prosthetic arm. The preferred lock connects the distal end of the liner to the distal end of the socket, but the invented lock may be used in locations and positions on the liner and socket other than the distal ends/regions. The preferred distal lock is adapted to limit, and more preferably to prevent, air flow into the hard socket through the distal lock mechanism, even in instances wherein a vacuum pump is operated to create/maintain significant vacuum inside the socket. The preferred distal lock comprises a latch/unlatching system that is comfortable and convenient for the wearer, wherein swinging a latch handle unlatches the liner from the lock without any need for the user to push or pull a plunger or shaft.

Because the invented distal lock effectively limits or prevents air flow through the lock mechanism to the hard socket, the pressure in the hard socket, between the socket interior wall and the liner, may be controlled reliably and predictably by preferred pressure-control means, such as automatic or manual air valves in air-communication with the hard socket interior and/or vacuum pumps, for example. The preferred embodiment is particularly beneficial in vacuum suspension systems, herein defined as systems wherein pressure inside the well of the hard socket is desired to be at least 5 psi less than ambient air pressure, and more preferably 5-14.7 psi less than ambient air pressure. This is because, with such a relatively low pressure inside the hard socket, there is a large driving force that would cause air flow into the hard socket through the distal lock, were it not effectively sealed. The preferred distal lock embodiment is effectively sealed, however, and in a way wherein lower pressure inside the hard socket actually tends to improve the seal of the distal lock, in effect, by pulling the sliding shaft and blade members inward toward the pin of the roll-on liner and keeping the sealing member against the sealing surface. With the variable of air flow through the distal lock eliminated by the preferred distal lock structure and operation, prosthetic technicians may focus on pressure/suction control by accurate valves and/or pumps specifically designed only for such control.

The preferred embodiments of the invented distal lock comprise an axial bore in a lock housing that is adapted to be installed and secured in the distal end of the hard socket. A radial bore is also provided in the lock housing and intersects the axial bore. The axial bore is open, at its top, to the well of the hard socket, and a liner pin secured to the distal end of a roll-on liner may slide into the axial bore when the wearer dons the socket. The liner pin is locked in the axial bore by a lock blade or other protrusion that approaches the axial bore from the radial bore and engages the liner pin. Preferably, the liner pin has circumferential grooves or other indentations that each may receive the lock blade depending upon how far the liner-covered limb is inserted into the socket and the axial bore. The lock blade is captured in or on a shaft member that resides in the radial bore. When the distal lock is in the latched position, the lock blade protrudes far enough into the axial bore to contact and engage the liner pin by extending into one of said grooves/indentations, thus preventing upward axial movement of the pin relative to the axial bore, the housing, and, hence, the removal of the liner-covered limb from the hard socket.

The preferred distal lock is unlatched by a cam mechanism that requires the user/assistant to flip/swing a latch handle in a direction that is generally circumferential relative to the circumference of the hard socket and liner/limb, rather than requiring the user/assistant to radially push or pull a shaft. Said flipping/swinging requires little strength and little agility, and so it is convenient and comfortable even when the wearer must bend over to do it. This convenient and comfortable unlatching may be compared to the more difficult radial pushing of a shaft/plunger such as required in distal locks such as the U.S. Pat. No. 6,334,876 device (FIG. 4).

Another object of the preferred embodiment is that the distal lock remains in its latched position, which secures the liner pin to the socket and also blocks air flow into and out of the hard socket, even during portions of the gait when additional force is exerted on the limb/liner relative to the hard socket and even if vacuum is established in the socket by a vacuum pump. Vacuum inside the hard socket tends to seat the air seal of the distal lock more firmly, rather than weakening or dislodging it.

Another object of the preferred embodiment is that the liner pin may be inserted and locked into the distal lock, without the distal lock being unlatched. This is accomplished by the lock blade being slidable relative to the lock shaft, toward and away from the axial bore in a direction parallel to the length of the shaft and the length of the radial bore. The lock blade is biased toward the axial bore, but may slide out of the way of the axial bore as described below. The lock blade is shaped so that, with the distal lock in the latched position, a liner pin entering the axial bore and impacting the blade will hit a tapered/slanted upper blade surface, and the blade will be temporarily pushed away from the axial bore to allow the pin to continue entering the axial bore. Once the liner pin rests inside the axial bore, the bias applied to the blade will then force the blade again toward the axial bore, to engage the pin in one or another of its grooves/recesses. Thus, the preferred liner pin may slide down the axial bore, pushing the blade out of the way enough to allow the liner pin to pass without damage to the pin or the blade. When the pin stops movement relative to the distal lock, the blade will "snap" into place engaging the pin, locking the pin from being withdrawn in the upward direction, that is, opposite that in which it entered. The blade, therefore, is tapered/slanted on its top surface, to allow downward movement of the pin when entering the axial bore, but the blade is not tapered/slanted in such a way on its lower surface. Pulling the pin up, therefore, does not tend to push the blade out of the way, and removing the liner pin up out of the lock is therefore not possible when the distal lock engaged (latched).

Another object of the preferred embodiment is that the distal lock is compact and does not require elements that protrude a significant distance from the circumference of the lock housing during normal use of the lock in its latched state. When the lock is unlatched, the latch handle does protrude radially outward a significant distance, but, as soon as the lock is latched, the handle resides against and/or near the outer surface of the lock housing.

BRIEF DESCRIPTION OF THE DRAWINGS

FIG. 1 is a side view of an example of a leg prosthesis, with a roll-on liner installed on the residual limb, the liner-covered limb inserted into the hard socket, and the prosthesis including a foot portion (lower leg and foot).

FIG. 2 is an example of a prior art hard socket (with liner shown inside the socket), which includes a distal lock incorporated into the distal end of the socket. This distal lock is of the type disclosed in Perkins U.S. Pat. No. 6,334,876, wherein inward, radial pushing of the plunger/shaft is done by the wearer or other person to unlatch the distal lock to release the liner from the socket.

FIG. 3 illustrates in cross-section an example roll-on liner, with a threaded fitting secured in the distal end of the liner for installation of a liner pin. Securement of the threaded fitting to the liner may be done by various conventional methods.

FIG. 4 is an exploded view of the distal lock of FIG. 2, with notes showing that action of plunger P according to Arrow A is caused by the spring bias, and it is against this spring bias that the wearer/assistant must push the plunger radially inward to unlatch the distal lock. Action according to Arrow B is caused in the event vacuum is established inside the hard socket, as the vacuum causes inward force that acts against the bias of the spring and serves to unseat the o-ring O. This is why this distal lock is not convenient or operable for prosthetics wherein significant vacuum is desired inside the hard socket; this distal lock, in effect, works against, and substantially prevents, vacuum being established in the hard socket.

FIGS. 5 and 6 are a top perspective view, and a top view, respectively, of the preferred distal lock of the invention. The preferred cammed latch handle may be swung approximately 90 degrees, from its position shown in FIG. 6 to a radial-extending position, which will pull the shaft outward to unlatch the lock.

FIG. 7A is a side-cross-sectional view of the preferred distal lock of FIGS. 5 and 6, showing the lock in the latched (engaged) position, viewed along the line 7A-7A in FIG. 6.

FIG. 7B is a top perspective view of the distal lock of FIGS. 5-7A, shown with the cammed latch handle swung approximately 90 degrees to unlatch (disengage) the lock.

FIG. 7C is a side-cross-sectional view of the distal lock of FIG. 7B, with distal lock in the unlatched position. The cammed ends of the handle may be seen to be pressing against the lock body to pull the lock shaft outward.

FIGS. 8A-C are various views of the preferred distal lock of FIGS. 5-7C, all shown with the lock latched. FIG. 8A is a side view, FIG. 8B is a front view, and FIG. 8C is a bottom view. In FIGS. 8A and B, the liner pin normally attached to the liner threaded insert is shown installed in the distal lock (without the liner shown in the figures), so that the viewer may understand the location of the liner pin in the distal lock.

FIG. 10A is a perspective view, FIG. 10B is a side view, FIG. 10C is a rear view, FIG. 10D is a front view, and FIG. 10E is a cross-sectional view along the line 10E-10E in FIG. 10D.

FIG. 11A is a front-top perspective view. From the perspective of the position of the handle in FIG. 11A, FIGS. 11B-H are, respectively, a top-rear perspective view, a right edge view, a top view, a front view, a bottom view, a left side edge view, and a cross-sectional view along the line 11H-11H in FIG. 11G.

FIGS. 12A-E are various views and details of the preferred shaft of the distal lock. FIG. 12A is a perspective view, FIG. 12B is a front end view, FIG. 12C is a side view, FIG. 12D is a top view, and FIG. 12E is a cross-sectional view along 12E-12E in FIG. 12D.

FIGS. 13A-G are various views and details of the preferred lock blade that is slidably (with spring-bias) connected to the shaft of FIGS. 12A-E, and that engages the liner pin when the distal lock is in the latched position.

DETAILED DESCRIPTION OF THE PREFERRED EMBODIMENT

Figures 1, 3:
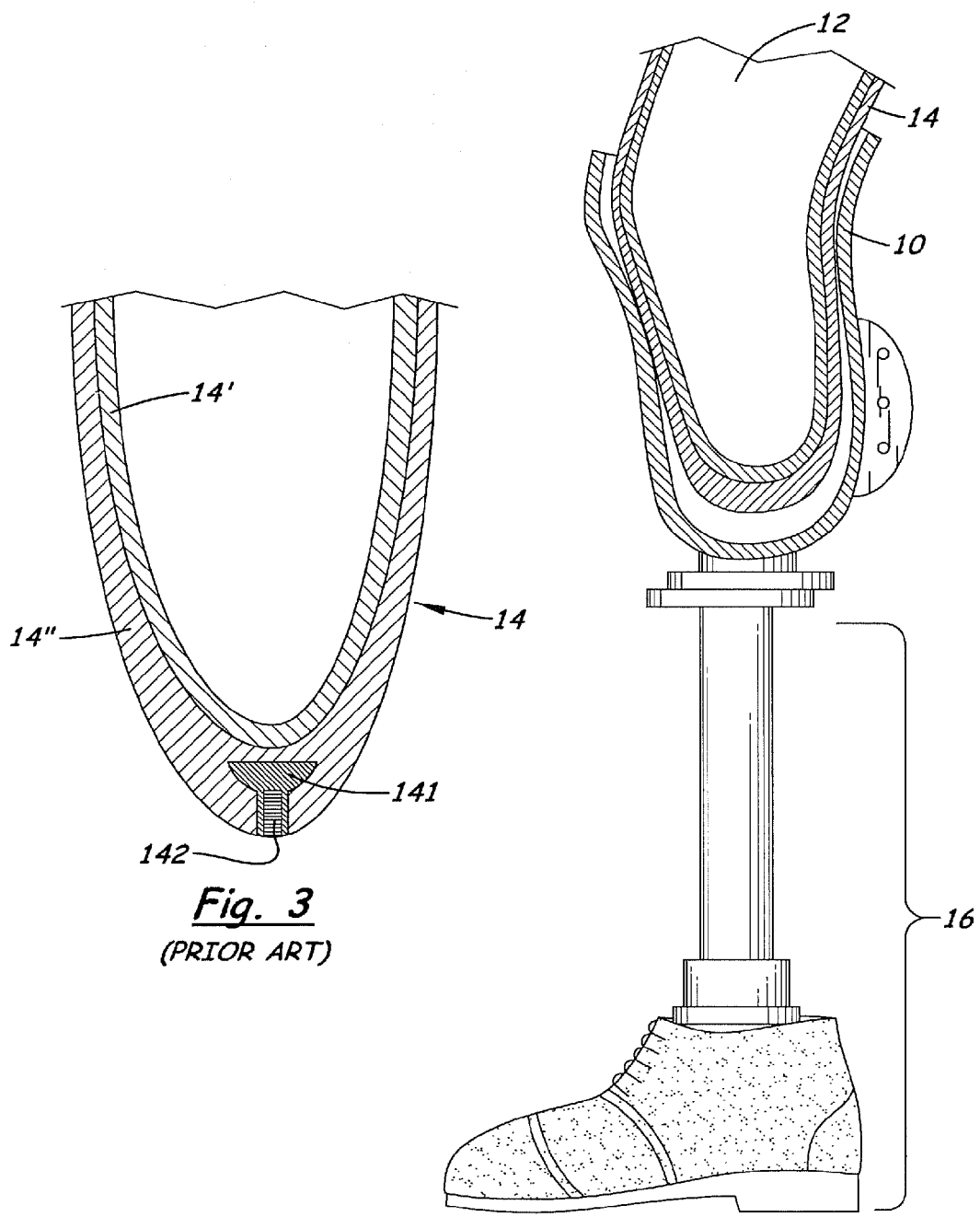
FIGS. 1-4 are various views of prior art prosthetic systems. Specifically.
Figure 2:
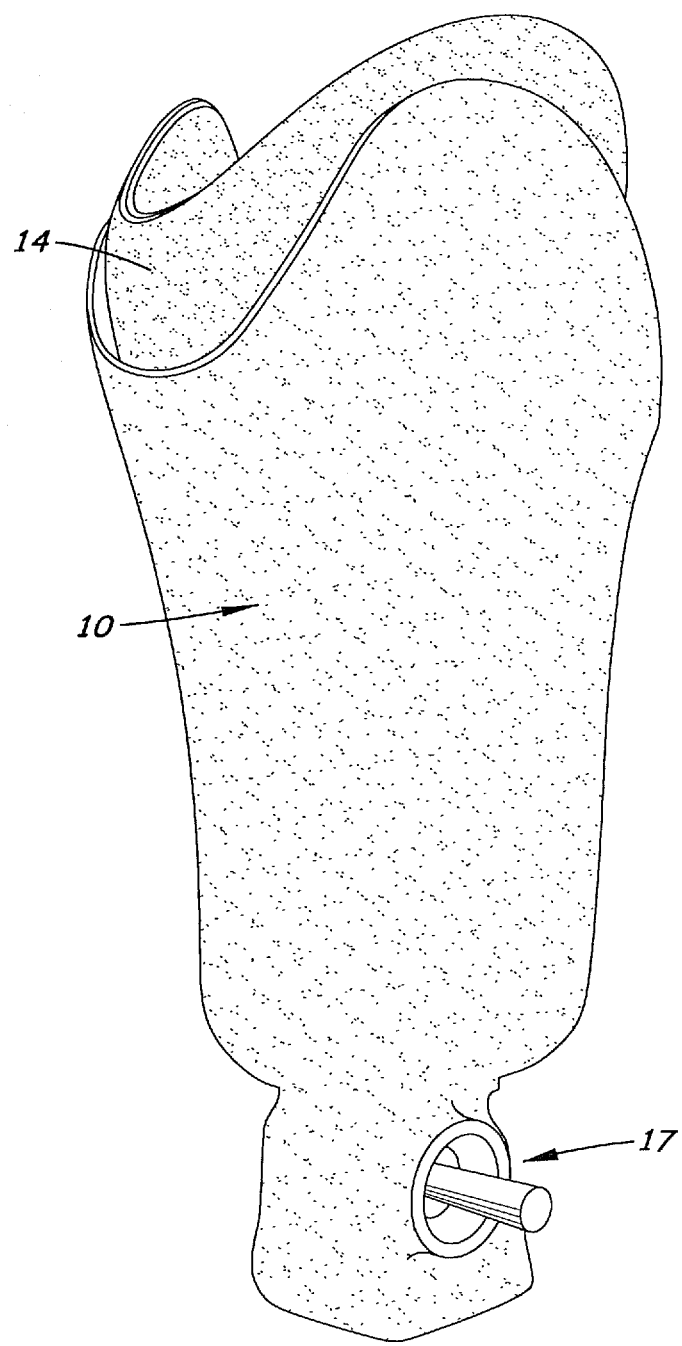
Figure 4:
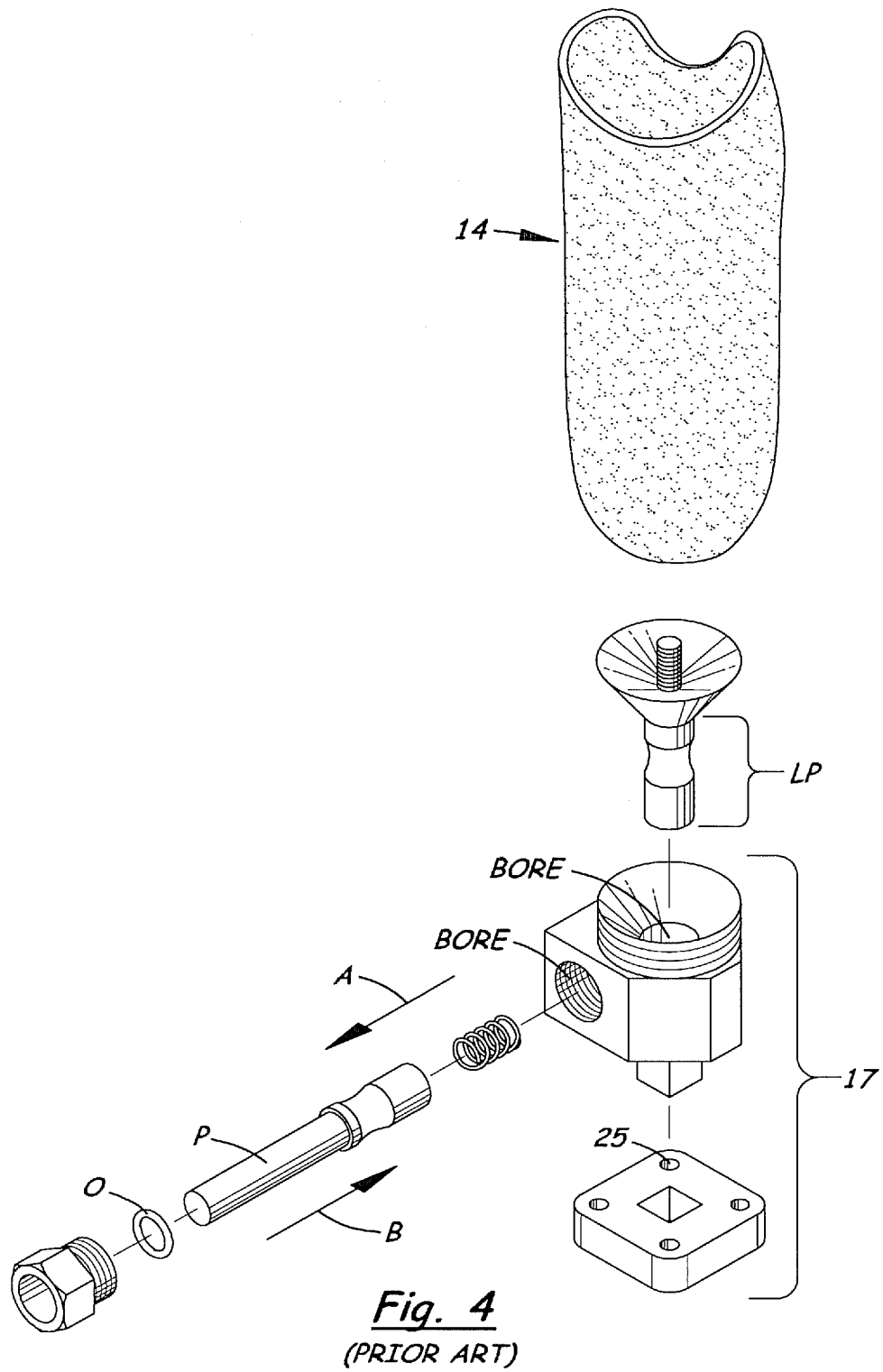
Figure 9A:
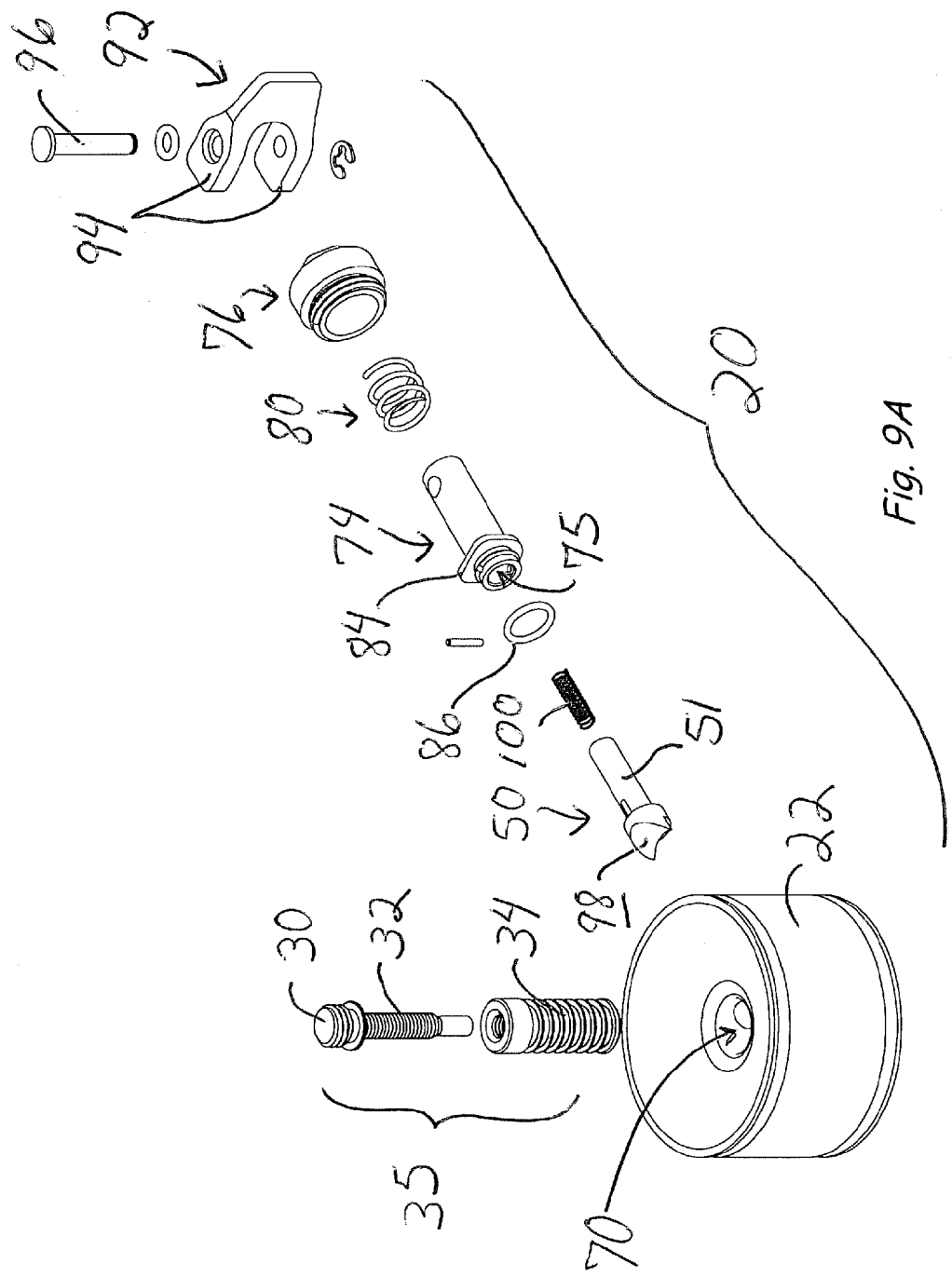
FIGS. 9A and B are exploded views of the preferred distal lock of FIGS. 5-8C, from two perspectives, with the multiple-component liner pin also shown exploded.
Figure 10D:
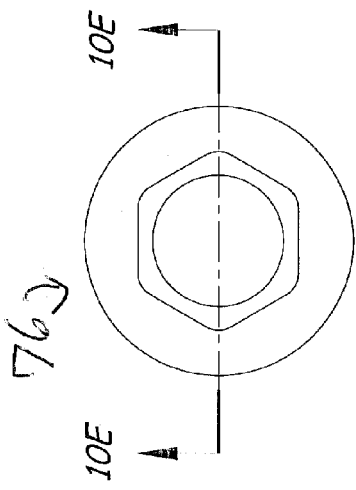
FIGS. 10A-E are various views and details of the preferred threaded body that attaches to the radial bore of the housing and through which the shaft slides.
Figure 10E:
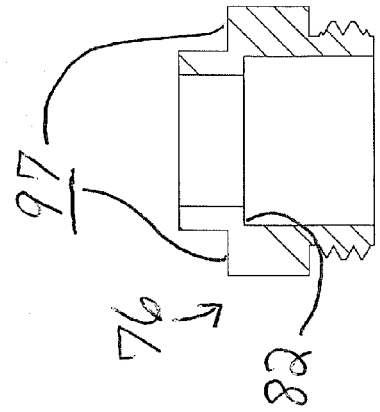
Figure 10B:
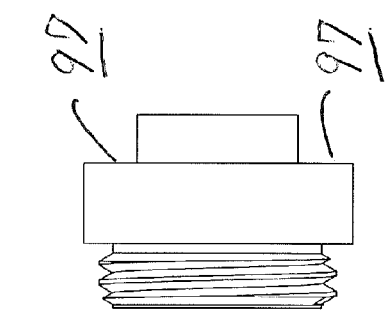
Figure 10A:
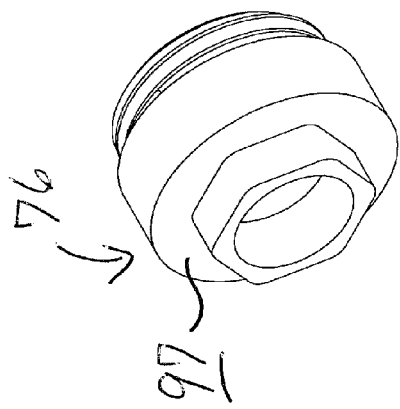
Figure 10C:
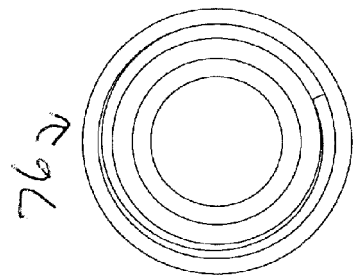
Figure 11A:
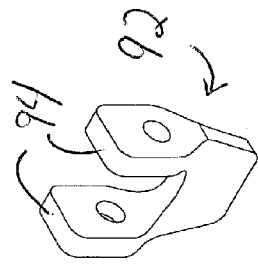
FIGS. 11A-H are various views and details of the preferred latch handle with cammed ends.
Figure 11C:
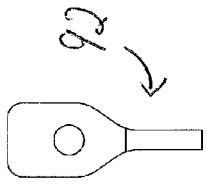
Figure 11B:
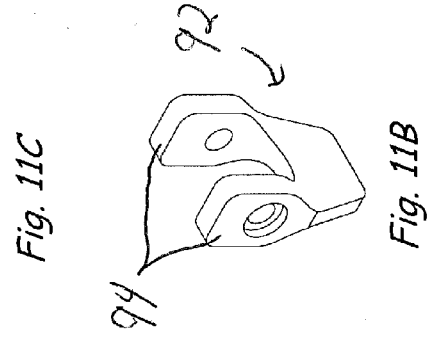
Figure 11D:
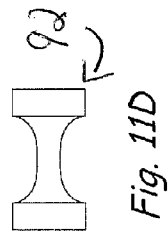
Figure 11E:
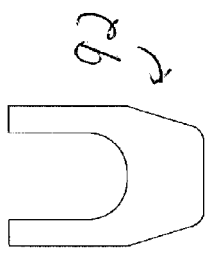
Figure 11F:
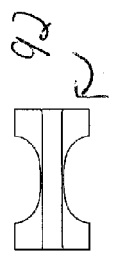
Figure 11G:
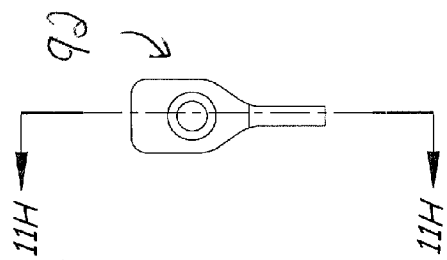
Figure 11H:
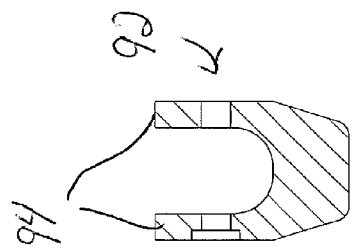

Referring to FIGS. 1-4, there are shown prior art systems for a leg prosthesis. Referring to FIGS. 5-13, there is shown one, but not the only, embodiment of the invented distal lock for a prosthetic limb hard socket. The preferred distal lock is especially beneficial for vacuum suspension, as it is adapted to block air flow through the distal lock unless and until the user or another person manually and purposely unlatches the distal lock. Alternatively, the distal lock, or adaptations of said distal lock, may be used for suction and/or other types of prosthesis suspension/connection, as desired by the wearer and/or judged optimal by the prosthetic technician.

FIGS. 1-4 illustrate schematically a hard socket 10, limb 12 with roll-on liner 14 (preferably with gel layer 14' and fabric layer 14"), and prosthetic foot portion 16. Connecting the foot portion 16 to the hard socket 10 is a distal lock 17, which may be molded into, or covered by, portions of the hard socket wall so that it is not visible in detail in/on the finished hard socket. The prior art distal lock 17 portrayed in FIGS. 1-4 is the prior art Perkins lock described above and is not conducive to use in prosthetic systems in which vacuum (typically 5-14.7 psi less than ambient) inside the hard socket is desirable. One may see piston P slides in direction A In FIGS. 5-13, an improved distal lock 20 is portrayed according to one embodiment of the invention. The distal lock housing 22 houses the main lock mechanism components, is molded into or otherwise connected to the hard socket, and also attaches to the foot portion 16. The upper surface 18 of the distal lock is preferably concave, for example, a conical or other curved shape, for a good fit and/or smooth transition between the surface 18 and the curved distal wall of the hard socket.

Many conventional liners 14 are manufactured with a 10 mm threaded hole at the longitudinal axis of the liner, in the distal end of the liner, as portrayed in the example shown in FIG. 3. Into this threaded hole is installed the threaded head 30 of preferred threaded shaft 32, which in turn is connected by a threaded connection to a larger-diameter pin sleeve 34. This assembly of shaft 32 and sleeve 34 may be considered the preferred "liner pin" 35 (see FIG. 9A); other liner pin styles and assemblies may be provided.

Pin sleeve 34 has multiple circular depressions spaced along its length, wherein each depression results in a protrusion 36 that has a radial top shelf surface 38 perpendicular to the length of the sleeve 34. Each protrusion 36 has a tapered/slanted bottom surface 40, which preferably slants in the range of 45-70 degrees from perpendicular to the length of the sleeve 34. It is these slanted bottom surfaces 40, interacting with the slanted top surface of the blade 50, that allow the sleeve 34 to push the tapered/slanted blade 50 out of the way while it slides down past the blade 50 during entry of the liner pin 35 into the latched lock.

The preferred liner pin 35, comprising threaded head 30 on shaft 32 plus sleeve 34, allows the lock pin to be adjustable in length to custom-fit each patient when necessary.

As shown to best advantage in FIG. 9B, axial bore 70 is provided preferably at the central longitudinal axis of the housing 22, and radial bore 72 extends into the housing from the preferably-cylindrical outer side wall. The two bores 70, 72 join at about midway in the housing 22, and it is in this junction that the lock blade 50 engages the sleeve 34.

Lock blade 50 is provided on the inner end of a radially-extending mechanism that extends from outside the housing 22 and through the radial bore 72 toward the axial bore 70. The radially-extending mechanism comprises a radial shaft 74 that slidably extends into the radial bore 72 through threaded body 76. Threaded body 76 connects to a threaded bore opening of the radial bore 72. A main spring 80 resides around shaft 74, with one end abutting an inner flange surface 82 of the body 76 (see FIG. 10E), and the opposite end abutting against the central flange 84 of the radial shaft 74 (see FIGS. 9A and 12E). This serves to bias the radial shaft 74 to slide in the radial bore toward the center of the housing 22, that is, toward the axial bore 70.

An o-ring 86 or other sealing member is provided on the inner surface (toward the axial bore 70) of the central flange 84, so that said biasing by the main spring 80 tends to force the o-ring 86 against an inner rim 90 of the radial bore (see FIGS. 7A and C). Thus, whenever the lock is in the "latched" position, the shaft 74 is slid inward to its full extent toward the axial bore. In this latched position, the main spring 80 biases the shaft 74 and o-ring 86 to air-seal the radial bore so that air does not flow past the o-ring and so does not flow from the outside through the radial bore and into the axial bore, and does not flow out of the axial bore through the radial bore to the outside.

The shaft 74 is sized in length relative to the inner rim 90 and the outer surface of the housing 22, and is connected to a latch handle 92 at its outer end in such a way that, when the latch handle is in the latched position, the blade extends a short distance into the axial bore 70, and the o-ring 86 seals against the inner rim 90, as shown in FIG. 7B. This is the position wherein the shaft 74 may be said to have "slid inward to its full extent toward the axial bore" and this is the position wherein the handle 92 extends generally circumferentially along and near the outer cylindrical surface of the housing 22.

From the latched condition, the lock may be unlocked or "unlatched" by swinging the handle 92 to a position wherein it extends radially outward away from the housing 22. See, for example, FIGS. 7B and C. The handle 92 comprises a cammed connection to the radial shaft 74, by cammed ends 94 rotating, on a pin 96 or other axle, so that the cammed ends 94 impact on and slide along outer flange surface 97 of the threaded body 76. Swinging the handle 92 to the radially-extending position forces, against the bias of the main spring 80, the radial shaft outward relative to the housing by means of the cammed ends moving on surface 97 (see FIGS. 10A, B, and E). This outward sliding/translation of the shaft 74 moves the o-ring away from the inner rim 90 of the bore 72 and pulls the blade 50 away from the sleeve 34 and out of the axial bore. This releases the sleeve 34, so that it (and the entire liner pin 35) may be pulled up and out of the axial bore 70 for allowing the socket to be removed from the liner-covered limb. The unsealing of the o-ring allows air flow into the radial bore and from there into the axial bore, which may help lessen vacuum inside the socket and, therefore, may help the wearer remove his/her liner-covered limb from the socket.

The blade 50 connection to the shaft 74 is adapted so that the liner pin 35 may be installed in the distal lock even if the distal lock is latched. The blade 50 is slidably connected to the shaft 74, by means of blade end 51 being received in a cavity 75 of the shaft 75, wherein the blade end 51 (and entire blade 50) can slide parallel, and coaxially, relative to the length of the shaft 74. A second spring 100 (see FIGS. 7A, 7C, 9A and B) is provided between the blade end 51, and an interior surface of the cavity 75 of shaft 74 to bias the blade relative to the shaft so that the blade tends to protrude farther from the shaft into the axial bore. Spring 100 is preferably centered along the longitudinal axis of the blade and the shaft by being received in a blade cavity 52, extending out of the cavity 52 to abut against an inner surface 77 of cavity 75. Thus, spring 100 biases surface 53 of the blade cavity 52 away from surface 77 of the shaft cavity 75 (see FIGS. 12E and 13 G). However, when the blade is pushed toward the shaft in the direction of the length of the shaft, the blade will slide to be closer to the shaft, that is, closer to the outer cylindrical surface of the housing. This biased, slidable connection of blade 50 to shaft 74 is further adapted by the blade 50 having a tapered/slanted upper surface 98. Edge 99 is curved on a radius approximately the same as the curvature of the recesses and corresponding protrusions 36 of the sleeve 34. This way, the edge 99, when latched into a recess of the sleeve 34, extends underneath a significant arc of the overhanging protrusion 36 and is not likely to slip relative to the sleeve and is not likely to break. Preferably, edge 99 extends 70-110 degrees along an arc generally centered at the longitudinal axis of the liner pin.

Interaction between the slanted bottom surfaces 40 of the protrusions of the sleeve 34 and the tapered/slanted upper surface 98 of the blade results in the force on the blade by the descending sleeve 34 having a significant radial vector (parallel to the radial bore and the shaft length). If the sleeve is pushed down into the axial bore with the lock latched, the slanted surfaces 40 of the sleeve protrusions 36 push on the tapered/slanted upper surface 98 of the blade, resulting in the blade moving parallel to the radial bore to temporarily be out of the way (outward deeper into the radial bore). After the sleeve 34 is inserted as far as dictated by the fit of the socket to the liner-covered limb, the sleeve 34 no longer pushes the blade out of the way, and the spring 100 urges the blade to engage the sleeve, and, therefore, to lock the sleeve inside the axial bore. Because of this system, the sleeve may be inserted whether or not the distal lock is latched, and the blade and lock mechanism is not damaged. The user may don the socket without having to unlatch or otherwise manipulate the distal lock.

Also, it may be noted that the slidable connection between the blade 50 and the shaft 74 allows the blade to move out of the way of the protrusions, by sliding outward relative to shaft 74, without breaking the vacuum seal provided by the shaft's o-ring 86 against surface 90. The blade moves out of the way of the pin system 35, while the shaft does not move (unless the user purposely unlatched the lock), so vacuum may be maintained inside the well of the socket, during donning and/or adjustment of the fit of the liner with the socket.

As discussed above in the Related Art and Summary sections, it is desirable that the preferred distal lock prevent air movement through the distal lock when it is latched. Lower pressure inside the socket relative to ambient, for example, as may be established by a vacuum pump connected to the inside of the socket, will further tend to keep the distal lock sealed against air flow. This is because vacuum inside the socket will tend to pull the lock shaft assembly toward the axial bore, pulling the o-ring into tighter sealing engagement against the inner rim of the radial bore. Thus, the preferred distal lock is well-adapted for vacuum suspension, and especially for one wherein it is desired to keep a substantial level of vacuum inside the socket, for example, 1-14.7 psi (and more preferably 5-14.7 psi) air pressure lower than ambient.

The main spring 80 is sized and of sufficient strength to maintain the o-ring in sealing position, whenever the distal lock is latched, even if there are pressure fluctuations in the hard socket due to the wearer's gait or for other reasons, and even if the pin assembly 35 moves downward relative to the blade 50 and hence moves the blade outward relative to the shaft. As discussed above, this special spring-biased, slidable blade feature maintains vacuum during relative motion of the pin assembly 35 and the blade 50 and during relative motion of the blade 50 and the shaft 74. The preferred device, and the vacuum in the socket, tend to maintain vacuum by maintaining the sliding members in the lock in an inward, sealed condition.

In some embodiments, the lock may be described as being for mounting on or in a prosthetic hard socket for connecting a roll-on liner on a residual limb to the hard socket, the lock system comprising: a housing having a first bore for receiving a pin of a roll-on residual limb liner and a second bore transverse and open to said first bore, the pin being slidable in said first bore and having a plurality of radial recesses; a shaft slidable in said second bore, having a first end extending into the housing and a second end extending out of the housing, and a longitudinal axis between said first end and said second end; a blade unit provided in said second bore and having a first blade end and a second blade end, wherein said blade first end extends into the first bore, and the second blade end is slidably connected to said shaft so that said blade unit slides relative to the shaft in a direction parallel to said longitudinal axis; a blade spring provided between the shaft and the blade unit, so that said blade unit is urged away from the shaft toward the first bore to engage at least one of said plurality of radial recesses of said pin; shaft spring adapted to urge the shaft into an inward lock-closed position, toward the first bore of the housing, wherein a seal provided on said first end of the shaft seals against a sealing surface of the housing when the shaft is in said lock-closed position; and a handle connected to the second end of the shaft and accessible at an outer surface of the housing, wherein said handle is adapted to pull the shaft outwards against the bias of the shaft spring into a lock-open position wherein the seal is moved away from the sealing surface to allow air to flow through the lock; and wherein said slidable connection of the blade unit to the shaft is adapted so that the blade slides outward relative to the shaft when outward force is applied to the blade unit, and the shaft and seal remain in lock-closed position to prevent air flow through the lock. The handle may be a lever pivotally connected to the shaft, and wherein said lever has at least one cammed end that pushes against the housing when the handle is swung to the lock-open position to pull the shaft outward from the housing. The housing may comprise a housing portion that comprises said first bore and said second bore and a threaded body portion that screws into the housing portion and through which the shaft passes for connection to the handle, wherein body portion comprises an outer surface against which the at least one cammed end pushes when the lever is swung to the lock-open position. The blade first end may have a curved edge for engaging said plurality of radial recesses of the pin. The blade first end may have a slanted upper surface against which protrusions of the pin push, when the pin moves downward into the first bore, to push the blade unit outward parallel to said longitudinal axis. The lever preferably swings close to an outside surface of the housing when in the lock-closed position, and swings about 90 degrees to extend out from the housing when in the lock-open position.

Other embodiments may be described as being for connecting a roll-on liner on a residual limb to a hard socket, and the lock system comprising: a roll-on liner comprising a pin having multiple radial protrusions and recesses between said protrusions; and a lock comprising: a housing having a first bore for receiving the pin and a second bore transverse and open to said first bore, the pin being slidable in said first bore; a shaft slidable in said second bore, having a first end extending into the housing and a second end extending out of the housing, and a longitudinal axis between said first end and said second end; a blade unit provided in said second bore and having a first blade end and a second blade end, wherein said blade first end extends into the first bore, and the second blade end is slidably connected to said shaft so that said blade unit slides relative to the shaft in a direction parallel to said longitudinal axis; a blade spring provided between the shaft and the blade unit, so that said blade unit is urged away from the shaft toward the first bore to engage at least one of said plurality of radial recesses of said pin; a shaft spring adapted to urge the shaft into an inward lock-closed position, toward the first bore of the housing, wherein a seal provided on said first end of the shaft seals against a sealing surface of the housing when the shaft is in said lock-closed position; and a handle connected to the second end of the shaft and accessible at an outer surface of the housing, wherein said handle is adapted to pull the shaft outwards against the bias of the shaft spring into a lock-open position wherein the seal is moved away from the sealing surface to allow air to flow through the lock; and wherein said slidable connection of the blade unit to the shaft is adapted so that the blade slides outward relative to the shaft when outward force is applied to the blade unit by the pin moving downward in the first bore, and the shaft and seal remain in lock-closed position to prevent air flow through the lock.

Other embodiments may be described as lock system for connecting a roll-on liner on a residual limb to a hard socket, the lock system comprising: a roll-on liner comprising a pin having multiple radial protrusions and recesses between said protrusions; and a lock that receives said pin in a first bore and comprises a second bore perpendicular to the first bore, wherein the lock further comprises: a shaft and blade unit provided in the second bore and biased inward toward the first bore to a lock-closed position, the shaft and blade unit comprising a blade slidably connected to a shaft, wherein the blade and shaft are biased away from each other by a blade spring; a seal on the shaft and blade unit adapted to seal against a sealing surface of the second bore when the lock is in the lock-closed position; and a handle connected to the shaft and adapted to pull the shaft outward into a lock-open position wherein the seal is distanced from the sealing surface so that air flows through the lock; wherein, when said pin is pushed downward in the first bore, said protrusions push the blade outward toward the shaft against the bias of the blade spring, and said shaft does not slide outward in the second bore, due to the slidable connection of said blade and shaft, and said seal remains sealed against the sealing surface.

Other embodiments are described as a lock system for connecting a roll-on liner on a residual limb to a hard socket, the lock system comprising: a roll-on liner comprising a pin; a lock that receives said pin in a first bore and comprises a second bore perpendicular to the first bore, wherein the lock further comprises: a shaft and blade unit provided in the second bore and biased inward toward the first bore to a lock-closed position wherein a seal on the unit seals against a sealing surface of the bore to prevent air flow through the lock and wherein the blade engages the pin to retain the pin in the first bore; a lever handle connected to the shaft and adapted to pull the blade and shaft unit outward from the first bore into a lock-open position wherein the seal is distanced from the sealing surface so that air flows through the lock and the blade disengages from the pin to allow the pin to be removed upward up out of the first bore. The lever handle preferably swings about 90 degrees to move the blade and shaft unit from the lock-closed position to the lock-open position. The blade and shaft unit may be comprised of a blade slidably connected to a shaft slidably, and the lever handle has at least one cammed portion that is pivotally connected to the shaft, wherein, when the lever handle is swung to the lock-open position, the cammed portions push against a surface of a portion of lock housing, to pull the shaft outward from the housing. The blade has an outer end that is received in a longitudinal shaft cavity of the shaft, the blade outer end has a longitudinal blade cavity, and the shaft and blade are biased away from each other by a blade spring received in the blade cavity and pressing against a surface of the shaft cavity. The pin may comprise an inner pin and a pin sleeve that surrounds the inner pin, said pin sleeve having comprising radial protrusions and recesses between the protrusions, wherein said inner pin is threaded for connection to a roll-on liner.

Other embodiments of the lock system may be described as comprising: a housing having a first bore at or near a center region of the housing, a second bore that is perpendicular to the first bore, and an elongated sliding unit; the sliding unit comprising an inner blade portion that engages a roll-on liner pin received in the first bore to retain the pin in the first bore, the sliding unit being received in said second bore and biased inward toward the first bore so that the sealing member seals against the second bore to prevent air flow from outside the housing through the second bore and into the first bore (and hence into the hard socket); the lock system further having a handle connected to the sliding member to pull the sliding member outward from the housing to unseal the sealing member and allow air to flow from outside the housing, through the second bore and into the first bore. The handle may be a lever that swings relative to the housing, and said lever having a cammed surface that pushes against the housing to pull the sliding member outward from the housing. The sliding member has an outer portion to which the lever is connected, the inner blade portion is slidably connected to said outer portion, and a spring urges the inner blade portion away from outer portion, and wherein the outer portion and seal remain in place to seal air from flowing into the lock, when the blade portion is forced toward the outer portion by the roll-on liner pin moving downward in the first bore.

Although this invention has been described above with reference to particular means, materials and embodiments, it is to be understood that the invention is not limited to these disclosed particulars, but extends instead to all equivalents within the broad scope of the following claims.

We claim:

1. A lock system for connecting a roll-on liner on a residual limb to a hard socket, the lock system comprising:
   a roll-on liner comprising a pin having multiple radial protrusions and recesses between said protrusions; and
   a lock comprising:
   a housing having a first bore for receiving the pin and a second bore transverse and open to said first bore, the pin being slidable in said first bore;
   a shaft slidable in said second bore, having a first end extending into the housing and a second end extending out of the housing, and a longitudinal axis between said first end and said second end;
   a blade unit provided in said second bore and having a first blade end and a second blade end, wherein said blade first end extends into the first bore, and the second blade end is slidably connected to said shaft so that said blade unit slides relative to the shaft in a direction parallel to said longitudinal axis;
   a blade spring provided between the shaft and the blade unit, so that said blade unit is urged away from the shaft toward the first bore to engage at least one of said plurality of radial recesses of said pin;
   a shaft spring adapted to urge the shaft into an inward lock-closed position, toward the first bore of the housing, wherein a seal provided on said first end of the shaft seals against a sealing surface of the housing when the shaft is in said lock-closed position;
   a handle connected to the second end of the shaft and accessible at an outer surface of the housing, wherein said handle is adapted to pull the shaft outwards against the bias of the shaft spring into a lock-open position wherein the seal is moved away from the sealing surface to allow air to flow through the lock; and
   wherein said slidable connection of the blade unit to the shaft is adapted so that the blade slides outward relative to the shaft when outward force is applied to the blade unit by the pin moving downward in the first bore, and the shaft and seal remain in lock-closed position to prevent air flow through the lock.

2. A lock system as in claim 1, wherein the handle is a lever pivotally connected to the shaft, and wherein said lever has at least one cammed end that pushes against the housing when the handle is swung to the lock-open position to pull the shaft outward from the housing.

3. A lock system as in claim 2, wherein said housing comprises a housing portion that comprises said first bore and said second bore and a threaded body portion that screws into the housing portion and through which the shaft passes for connection to the handle, wherein body portion comprises an outer surface against which the at least one cammed end pushes when the lever is swung to the lock-open position.

4. A lock system as in claim 1, wherein the blade first end has a curved edge for engaging said recesses of the pin.

5. A lock system as in claim 1, wherein the blade first end has a slanted upper surface against which protrusions of the pin push, when the pin moves downward into the first bore, to push the blade unit outward parallel to said longitudinal axis while maintaining the seal against the sealing surface.

6. A lock system for connecting a roll-on liner on a residual limb to a hard socket, the lock system comprising:
   a roll-on liner comprising a pin having multiple radial protrusions and recesses between said protrusions; and
   a lock that receives said pin in a first bore and comprises a second bore perpendicular to the first bore, wherein the lock further comprises:
   a shaft and blade unit provided in the second bore and biased inward toward the first bore to a lock-closed position, the shaft and blade unit comprising a blade slidably connected to a shaft, wherein the blade and shaft are biased away from each other by a blade spring;
   a seal on the shaft and blade unit adapted to seal against a sealing surface of the second bore when the lock is in the lock-closed position;
   a handle connected to the shaft and adapted to pull the shaft outward into a lock-open position wherein the seal is distanced from the sealing surface so that air flows through the lock;
   wherein, when said pin is pushed downward in the first bore, said protrusions push the blade outward toward the shaft against the bias of the blade spring, and said shaft does not slide outward in the second bore, due to the slidable connection of said blade and shaft, and said seal remains sealed against the sealing surface.

7. A lock system for connecting a roll-on liner on a residual limb to a hard socket, the lock system comprising:
   a roll-on liner comprising a pin;
   a lock that receives said pin in a first bore and comprises a second bore perpendicular to the first bore, wherein the lock further comprises:
   a shaft and blade unit provided in the second bore and biased inward toward the first bore to a lock-closed position wherein a seal on the unit seals against a sealing surface of the bore to prevent air flow through the lock and wherein the blade engages the pin to retain the pin in the first bore;
   a lever handle connected to the shaft and adapted to pull the blade and shaft unit outward from the first bore into a lock-open position wherein the seal is distanced from the sealing surface so that air flows through the lock and the blade disengages from the pin to allow the pin to be removed upward up out of the first bore.

8. A lock system as in claim 7, wherein lever handle swings about 90 degrees to move the blade and shaft unit from the lock-closed position to the lock-open position.

9. A lock system as in claim 8, wherein the blade and shaft unit is comprised of a blade slidably connected to a shaft slidably, and the lever handle has at least one cammed portion that is pivotally connected to the shaft, wherein, when the lever handle is swung to the lock-open position, the cammed portions push against a surface of a portion of lock housing, to pull the shaft outward from the housing.

10. A lock system as in claim 7, wherein the blade has an outer end that is received in a longitudinal shaft cavity of the shaft, the blade outer end has a longitudinal blade cavity, and the shaft and blade are biased away from each other by a blade spring received in the blade cavity and pressing against a surface of the shaft cavity.

11. A lock system as in claim 7, wherein the blade has a curved innermost edge that engages the pin when the lock is in the lock-closed position.

12. A lock system as in claim 11, wherein the blade has a slanted upper surface which is slanted upward away from the first bore, so that the slanted upper surface is forced outward from the pin when protrusions of the pin impact said slanted upper surface.

13. A lock system as in claim 7, wherein said pin comprises an inner pin and a pin sleeve that surrounds the inner pin, said pin sleeve having radial protrusions and recesses between the protrusions, wherein said inner pin is threaded for connection to a roll-on liner.

14. A lock system comprising:
a roll-on liner comprising a pin; and
a lock comprising:
a housing having a first bore at or near a center region of the housing, a second bore that is perpendicular to the first bore, and an elongated sliding unit;
the sliding unit comprising an inner blade portion that engages the liner pin received in the first bore to retain the pin in the first bore, the sliding unit being received in said second bore and biased inward toward the first bore so that a sealing member seals against the second bore to prevent air flow from outside the housing through the second bore and into the first bore; and
the lock system further having a handle connected to the sliding unit to pull the sliding unit outward from the housing to unseal the sealing member and allow air to flow from outside the housing, through the second bore and into the first bore.

15. A lock system as in claim 14, wherein the handle is a lever that swings relative to the housing, and said lever having a cammed surface that pushes against the housing to pull the sliding unit outward from the housing.

16. A lock system as in claim 14, wherein the liner pin comprises multiple radial protrusions and recesses between said protrusions, and a blade end has a curved edge for engaging the recesses in the pin.

17. A lock system as in claim 14, wherein the sliding unit has an outer portion to which the lever is connected, the inner blade portion is slidably connected to said outer portion, and a spring urges the inner blade portion away from outer portion, and wherein the outer portion and seal remain in place to seal air from flowing into the lock, when the blade portion is forced toward the outer portion by the roll on liner pin moving downward in the first bore.

* * * * *